United States Patent [19]

Van Berkel et al.

[11] 4,234,512

[45] Nov. 18, 1980

[54] CYCLOPROPANE DERIVATIVES

[75] Inventors: Johannes Van Berkel; Hendrik C. Kelderman, both of Amsterdam, Netherlands

[73] Assignee: Shell Oil Company, Houston, Tex.

[21] Appl. No.: 55,857

[22] Filed: Jul. 9, 1979

[30] Foreign Application Priority Data

Jul. 19, 1978 [GB] United Kingdom ............... 30338/78
Jul. 19, 1978 [GB] United Kingdom ............... 30340/78

[51] Int. Cl.$^3$ .................. C07C 47/293; C07C 43/305
[52] U.S. Cl. .................................... 568/420; 568/591; 564/12
[58] Field of Search ......................... 260/598; 568/591

[56] References Cited

U.S. PATENT DOCUMENTS

| | | | |
|---|---|---|---|
| 3,673,256 | 6/1972 | Pieper et al. | 260/598 |
| 4,024,163 | 5/1977 | Elliott et al. | 260/347.4 |

OTHER PUBLICATIONS

Ratcliffe et al., Jour. Org. Chem., vol. 35, No. 11 (1970), 4000–4002.
Corey et al., Tetrahedron Letters, No. 31 (1975) 2647–2650.
Lavielle et al., Bull. Soc. Chim. Fr., No. 6 (1971) 2047–2053.
Combret et al., Tetrahedron Letters, No. 15 (1971) 1035–1038.
Ried et al., Ann. der Chemie, vol. 679 (1964) 51–55.
Castro et al., Bull. Soc. Chim. Fr., No. 8 (1969) 2770–2773.
Castro et al., C. R. Acad. Sc. Paris, vol. 268, Series C (1969) 1067–1069.
Salmond, Tetrahedron Letters, No. 14 (1977) 1239–1240.

*Primary Examiner*—Bernard Helfin

[57] ABSTRACT

2-(2,2-Dimethoxyethyl-3,3-dimethylcyclopropanecarbaldehyde and 2-[2-(2,2-dihalovinyl)-3,3-dimethylcyclopropyl]ethanal dimethyl acetals are new pyrethroid intermediates. They are prepared from 2-(2-hydroxymethyl-3,3-dimethylcyclopropyl)ethanal dimethyl acetal.

5 Claims, No Drawings

CYCLOPROPANE DERIVATIVES

BACKGROUND OF THE INVENTION

Field of the Invention

The present invention is directed to new cyclopropane derivatives, their preparation and their use as intermediates in the preparation of certain synthetic pyrethroids.

SUMMARY OF THE INVENTION

The invention relates to the new chemical compound, 2-(2,2-dimethoxyethyl)-3,3-dimethylcyclopropanecarbaldehyde having the formula I

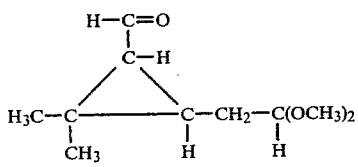
(I)

which is a useful intermediate in the preparation of pyrethroid ester pesticides of 2-(2,2-dihalovinyl)-3,3-dimethylcyclopropanecarboxylic acid as described in U.S. Pat. No. 4,024,163.

This invention also provides a process for the preparation of 2-(2,2-dimethoxyethyl)-3,3-dimethylcyclopropanecarbaldehyde, which comprises reacting 2-(2-hydroxymethyl-3,3-dimethylcyclopropyl)ethanal dimethyl acetal of the formula II

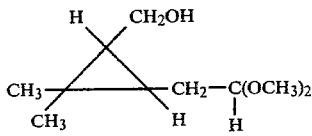
(II)

with a compound capable of oxidizing the hydroxymethyl group in a primary alcohol of a formyl group. A convenient manner is oxidation, for example, with the chromium trioxide-pyridine complex or with pyridinium chlorochromate, as described in J. Org. Chem. 35 (1970) No. 11, 4000–4002 and Tetrahedron Letters 31 (1975) 2647–2650. Another method for this conversion is catalytic dehydrogenation, for example, in the presence of a copper chromite catalyst. Methods for conversion of a hydroxymethyl group into a formyl group can be found in "Methoden der organischen Chemie" (Houben-Weyl), Volume VII, Part 1 (1954), 159–192. When starting from the (1R,cis) isomer of the hydroxymethyl substituted ethanal dimethyl acetal, the process according to the invention affords the carbaldehyde exclusively in the (1R,cis) configuration.

The invention also provides a process for the preparation of 2-[2-(2,2-dihalovinyl)-3,3-dimethylcyclopropyl]ethanal dimethyl acetal having the formula III

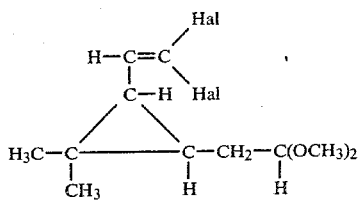
(III)

wherein each Hal independently is a chlorine, fluorine or bromine atom, which process comprises two steps, the first step consisting in reaction of a tri(dialkylamino) phosphine or an alkyl ester of an ortho-phosphorous acid bis(dialkylamide) with a compound generating a dihalocarbene—which reaction is allowed to proceed to virtual completion—and the second step with 2-(2,2-dimethoxyethyl)-3,3-dimethylcyclopropanecarbaldehyde, both steps being carried out in the presence of a solvent.

Suprisingly, the two-step process according to the present invention affords 2-[2-(2,2-dihalovinyl)-3,3-dimethylcyclopropyl]ethanal dimethyl acetal in a considerably higher yield than a one-step process comprising reaction of 2-(2,2-dimethoxyethyl)-3,3-dimethylcyclopropanecarbaldehyde, a tri(dialkylamino)phosphine or an alkyl ester of an ortho-phosphorous acid bis(dialkylamide) and a compound generating a dihalocarbene.

The alkyl groups present in the tri(dialkylamino)phosphine or the alkyl ester of an ortho-phosphorous acid bis(dialkylamide) may be the same or different and linear or branched. The alkyl groups are suitably the same, they have preferably fewer than six, and more preferably fewer than three carbon atoms. The use of tri(dialkylamino)phosphines is preferred, because they usually afford the desired 2-[2-(2,2-dihalovinyl)-3,3-dimethylcyclopropyl]ethanal dimethyl acetal in a higher yield than the alkyl esters of ortho-phosphorous acid bis(dialkylamides) (the latter compounds are obtained by replacing one of the dialkylamino groups in a tri(dialkylamino)phosphine by an alkoxy group). Tri(diethylamino)phosphine and tri(dimethylamino)phosphine are most preferred.

Tri(dialkylamino)phosphines may easily be prepared by reaction of a dialkylamine with a phosphorous trihalide, as described in "Organic Synthesis", Coll. Vol. V (1973) 602–603. This reaction results in the formation of a solution of the tri(dialkylamino)phosphine which also contains precipitated dialkylammonium halide. Filtration of the precipitate and distillation of the filtrate yields as a fraction pure tri(dialkylamino)phosphine. Applicant has tried to avoid the preparation of pure tri(dialkylamino)phosphine by contacting the solution containing the precipitate or the solution obtained after filtration of the precipitate, with 2-(2,2-dimethoxyethyl)-3,3-dimethylcyclopropanecarbaldehyde, but this procedure affords only a very small amount of the desired 2-[2-(2,2-dihalovinyl)-3,3-dimethylcyclopropyl]ethanal dimethyl acetal, if any. It has now been found that this solution itself contains compounds which prevent the reaction of 2-(2,2-dimethoxyethyl)-3,3-dimethylcyclopropanecarbaldehyde and that these compounds can easily be removed. Accordingly, a preferred embodiment of the present invention comprises reacting a dialkylamine with a phosphorous trihalide in the presence of a solvent that is substantially inert, washing the resulting reaction mixture with water (whether or not after prior separation of the precipitated dialkylammonium halide) and reacting the tri(-dialkylamino)phosphine dissolved in the washed solution with the compound generating a dihalocarbene. This embodiment usually affords 2-[2-(2,2-dihalovinyl)-3,3-dimethylcyclopropyl]ethanal dimethyl acetal in high yield. It is not necessary to separate the precipitated dialkylammonium halide prior to washing, because this salt is water soluble. The yield of the desired acetal can further be enhanced by drying the washed liquid, for example over a solid drying agent such as anhydrous sodium sulphate or anhydrous magnesium sulphate.

Another attractive feature of the process according to the present invention is that it may be carried out in the presence of alkane solvents, for example in alkane solvents with a boiling point or boiling range up to 200° C. This also applies to the said reaction between a dialkylamine and a phosphorous trihalide. Examples of alkane solvents are pentane, hexane, heptane, octane and nonane. Mixtures of alkanes are very suitable, for example, gasolines having a boiling range from 62° C. to 82° C. or from 80° C. to 110° C. If desired, the process may be carried out in substantially inert solvents other than alkanes, for example, in tetrahydrofuran.

Examples of compounds generating a dihalocarbene under the conditions of the process according to the present invention are carbon tetrahalides, chloroform, bromoform and iodoform. Examples of carbon tetrahalides are carbon tetrachloride, carbon tetrabromide, carbon tetraiodide, bromotrichlormethane (forming dichlorocarbene) and dibromodifluoromethane (forming difluorocarbene). Very good results have been obtained with carbon tetrachloride.

Both steps of the process according to the present invention are preferably carried out at a temperature in the range of from −50° C. to +50° C., particularly at temperatures of from −20° C. to +35° C.

The process according to the invention may be carried out by adding a tri(dialkylamino)phosphine or an alkyl ester of an orthophosphorous acid bis(dialkylamide) to a compound generating a dihalocarbene, if desired dissolved in a solvent that is suitably inert, for example, in an alkane solvent and stirring the mixture thus obtained until the first step has been substantially completed, which may take from 1 to 60 minutes. Then, the carbaldehyde I is added to the mixture and stirring continued for 1 to 60 minutes until the second step has been completed. Dihalophosphoranes and phosphine oxides can be removed from the reaction mixture by washing. This washing can be carried out with water when tri(dimethylamino)phosphine has been used, but when a tri(dialkylamino)phosphine having two or more carbon atoms in the alkyl groups has been used, dilute aqueous hydrochloric acid is more suitable than water. Therefore, tri(dimethylamino)phosphine is the most preferred tri(dialkylamino)phosphine. The washed reaction mixture is dried and the solvent is evaporated from the dried solution to leave a residue, which may be further purified, for example by distillation, to give dihalovinyl-substituted ethanal dimethyl acetal III in a pure state.

The above carbaldehyde I and dihalovinyl-substituted ethanal dimethyl acetal III each have two asymmetric carbon atoms in the cyclopropane ring and, therefore, can have the (1R,cis), (1R,trans), (1S,cis) or (1S,trans) configuration. The nomenclature used herein to describe the spatial configurations has been defined by M. Elliott et al., in Nature, 248 (1974) 710–711.

Among the four spatial configurations of the above carbaldehyde I and ethanal dimethyl acetal III, the isomer with the (1R,cis) configuration is preferred, because among these four spatial configurations of the pyrethroid esters of 2-(2,2-dihalovinyl)3,3-dimethylcyclopropanecarboxylic acid, the esters with the (1R,cis) configuration have the highest pesticidal activity.

The hydroxymethyl-substituted ethanal dimethyl acetal II starting material for this process originates from the natural terpene, carene. Carene is first ozonized and the resulting product treated with dimethyl sulfide in methanol to form 2-[2-(2-oxopropyl)-3,3-dimethylcyclopropyl]ethanal dimethyl acetal which is oxidized to the corresponding methyl acetate. Hydrolysis of the acetate yields the 2-(2-hydroxymethyl-3,3-dimethylcyclopropyl)ethanal dimethyl acetal. These steps are described in copending U.S. patent application, Ser. No. 953,987, filed Oct. 23, 1978.

ILLUSTRATIVE EMBODIMENTS

The present invention is illustrated by the following embodiments which describe the preparation of typical species of the invention and should not be regarded as limiting the invention in any way. Yields and purities were determined by means of gas-liquid chromatography and nuclear magnetic resonance (NMR) spectroscopy. The NMR data quoted were recorded at 90 MHz using solutions of the compounds in deuterochloroform; the absorptions given are relative to a tetramethylsilane standard.

EMBODIMENT 1

(1R,cis)-2-(2,2-dimethoxyethyl)-3,3-dimethylcyclopropanecarbaldehyde

A solution of (1R,cis)-2-(2-hydroxymethyl-3,3-dimethylcyclopropyl)ethanal dimethyl acetal (84.8 mmol, obtained as described in copending U.S. patent application Ser. No. 953,987) in dichloromethane (80 ml) in a 500-ml flask. After stirring for three hours at 20° C. the black precipitate present in the reaction mixture was filtered off through Florisil (a trademark) and the precipitate was washed with three 50-ml portions of diethyl ether. The solvent was evaporated from the combined filtrates to give 100 ml of a residual liquid. This liquid was filtered through Florisil and the diethyl ether was evaporated from the filtrate (40° C./2 kPa) to give a residue (14.2 g containing 2-(2,2-dimethoxyethyl)-3,3-dimethylcyclopropanecarbaldehyde in 100% (1R,cis) configuration; purity 87%, yield 80.5%, determined by gas-liquid chromatography and nuclear magnetic resonance (NMR) spectroscopy). The NMR spectrum of this desired product showed the following absorptions (at 90 MHz, using a solution of the desired product in deuterochloroform and relative to a tetramethylsilane standard):

| | |
|---|---|
| $\delta$ = 1.22 ppm | singlet H$_3$C—C—CH$_3$ |
| $\delta$ = 2.03 ppm | double doublet HC—CH$_2$—CH |
| $\delta$ = 4.32 ppm | triplet (H$_3$C—O)$_2$—CH— |
| $\delta$ = 1.33 ppm | singlet H$_3$C—C—CH$_3$ |
| $\delta$ = 3.34 ppm | singlet H$_3$C—O—C—O—CH$_3$ | multiplets for the two H atoms bound to the ring.

EMBODIMENT II

(1R,cis)-2-[2-(2,2-Dichlorovinyl)-3,3-dimethylcyclopropyl]ethanal dimethyl acetal Tri(dimethylamino)phsophine (168.3 mmol) was added over a period of 12 minutes to a stirred solution of carbon tetrachloride 167.4 mmol) in pentane (360 ml) kept at 0° C. under nitrogen in a 1-liter flask. Then, the mixture in the flask was stirred for 30 minutes at 0° C. This finished the first step.

At 0° C., (1R,cis)-2-(2,2-dimethoxyethyl)-3,3-dimethylcyclopropanecarbaldehyde (66.4 mmol, obtained as in Embodiment I above) was added dropwise to the suspension in the flask over a period of nine minutes. The temperature was increased to 12° C. over a period of 15 minutes and stirring was continued at the temperature for a further 15 minutes. This finished the second step. Then, water (75 ml) was added at 12° C. and—after removal of the aqueous phase—the organic phase was washed with two 35-ml portions of water. The washed organic phase was dried over anhydrous magnesium sulphate and the solvent was evaporated from the dried solution to give a residue (17.4 g) containing 2-[2-(2,2-dichlorovinyl)-3,3-dimethylcyclopropyl]-ethanal dimethyl acetal (100% (1R,cis), purity 88%, yield 91.1%). The NMR spectrum for this desired product showed the following absorptions:

| | |
|---|---|
| δ = 1.00 ppm | singlet H$_3$C—C—CH$_3$ |
| δ = 3.33 ppm | singlet C—(O—CH$_3$)$_2$ |
| δ = 5.59 ppm | doublet C=C$\underline{H}$ |
| δ = 1.13 ppm | singlet $\underline{H}_3$C—C—CH$_3$ |
| δ = 4.33 ppm | triplet (H$_3$C—O)$_2$—C$\underline{H}$— | multiplets for the two H atoms bound to the ring and for HC—C$\underline{H}_2$—CH.

EMBODIMENT III

(1R,cis)-2-[2-(2,2-dichlorovinyl)-3,3-dimethylcyclopropyl]ethanal dimethyl acetal Tri(dimethylamino)phosphine (163.2 mmol) was added with stirring at 0° C. to a solution of (1R,cis)-2-(2,2-dimethoxyethyl)-3,3-dimethylcyclopropanecarbaldehyde (65.5 mmol) and carbon tetrachloride (163.2 mmol) in n-pentane (350 ml) kept under nitrogen in a 1-l flask. After 15 minutes stirring, the mixture was warmed up to 14° C. and kept at this temperature for 15 minutes. Then, water (75 ml) was added at 14° C. and—after removal of the aqueous phase—the organic phase was washed with two 35-ml portions of water. The washed organic phase was dried over anhydrous magnesium sulphate and the solvent was evaporated from the dried solution to give a residue (15.7 g) containing 32.1 mmol of 2-[2-(2,2-dichlorovinyl)-3,3-dimethylcyclopropyl]ethanal dimethyl acetal (100% (1R,cis), purity 51.7%, yield 49%).

Comparison with the yield of the same product obtained in Embodiment II shows that the two-step process of Embodiment II for the preparation 2-[2-(2,2-dichlorovinyl)-3,3-dimethylcyclopropyl]ethanal dimethyl acetal gives considerably high yields.

We claim:

1. 2-(2,2-Dimethoxyethyl)-3,3-dimethylcyclopropanecarbaldehyde.

2. The (1R,cis) isomer of the compound claimed in claim 1.

3. 2-[2-(2,2-Dihalovinyl)-3,3-dimethylcyclopropyl]ethanal dimethyl acetal wherein each halo independently is chloro, fluoro or bromo.

4. A diacetal according to claim 3 wherein each halo is chloro.

5. The (1R,cis) isomer of the compound claimed in claim 3.

* * * * *